(12) United States Patent
Javanmard

(10) Patent No.: US 11,099,145 B2
(45) Date of Patent: Aug. 24, 2021

(54) MULTIPLEXED ASSAYS

(71) Applicant: Rutgers, The State University of New Jersey, New Brunswick, NJ (US)

(72) Inventor: Mehdi Javanmard, West Windsor, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 428 days.

(21) Appl. No.: 16/069,590

(22) PCT Filed: Jan. 12, 2017

(86) PCT No.: PCT/US2017/013170
§ 371 (c)(1),
(2) Date: Jul. 12, 2018

(87) PCT Pub. No.: WO2017/123742
PCT Pub. Date: Jul. 20, 2017

(65) Prior Publication Data
US 2019/0017950 A1 Jan. 17, 2019

Related U.S. Application Data

(60) Provisional application No. 62/277,547, filed on Jan. 12, 2016.

(51) Int. Cl.
*G01N 27/00* (2006.01)
*G01N 27/02* (2006.01)
(Continued)

(52) U.S. Cl.
CPC ...... *G01N 27/026* (2013.01); *B01L 3/502753* (2013.01); *C23C 14/223* (2013.01);
(Continued)

(58) Field of Classification Search
CPC .......... G01N 27/026; G01N 33/54326; G01N 33/54346; G01N 27/00; G01N 27/02;
(Continued)

(56) References Cited

U.S. PATENT DOCUMENTS

2005/0221494 A1   10/2005 Natan
2006/0103840 A1   5/2006 Fritz et al.
(Continued)

*Primary Examiner* — Brian J. Sines
(74) *Attorney, Agent, or Firm* — Fox Rothschild LLP

(57) ABSTRACT

Systems and methods electronic barcoding of particles. The methods comprise: performing operations by a spin coater to spin coat a single layer of particles onto a substrate; performing operations by a heat applicator to apply heat to the substrate so as to evaporate a liquid; and performing operations by at least one material depositor to transform the particles into Electronically Barcoded Particles ("EBPs"). EBPs are fabricated by: coating a portion of each said particle of the particles with a first conductive layer; depositing an insulative layer on the first conductive layer; and/or depositing a second conductive layer on the insulative layer so as to form a parallel plate capacitor on the particle. The parallel plate capacitor is tuned so that the particle has a capacitance that is different than the capacitances of other ones of the electronically barcoded particles.

9 Claims, 13 Drawing Sheets

(51) Int. Cl.
*G01N 33/68* (2006.01)
*G01N 33/543* (2006.01)
*C23C 18/12* (2006.01)
*C23C 14/22* (2006.01)
*B01L 3/00* (2006.01)
*C23C 14/30* (2006.01)
*B05D 1/00* (2006.01)

(52) U.S. Cl.
CPC ..... *C23C 18/127* (2013.01); *G01N 33/54326* (2013.01); *G01N 33/54346* (2013.01); *B05D 1/005* (2013.01); *C12Q 2537/143* (2013.01); *C23C 14/30* (2013.01); *G01N 33/68* (2013.01)

(58) Field of Classification Search
CPC .... G01N 33/68; C23C 14/223; C23C 18/127; B05D 1/005; C12Q 2537/143
See application file for complete search history.

(56) References Cited

U.S. PATENT DOCUMENTS

| | | |
|---|---|---|
| 2010/0028453 A1 | 2/2010 | Yoo et al. |
| 2010/0075340 A1 | 3/2010 | Javanmard et al. |
| 2011/0186433 A1 | 8/2011 | Pollack et al. |
| 2011/0318535 A1 | 12/2011 | Jung et al. |
| 2013/0260113 A1 | 10/2013 | Hart |
| 2013/0293884 A1 | 11/2013 | Lee et al. |
| 2013/0316467 A1* | 11/2013 | Carron ................. G01N 21/658 436/501 |
| 2014/0154464 A1 | 6/2014 | Miller et al. |
| 2015/0258218 A1* | 9/2015 | Kircher .............. A61K 51/1251 424/1.29 |
| 2017/0266328 A1* | 9/2017 | Wall ................... A61K 51/1251 |

* cited by examiner

MULTIPLEXED ASSAYS

CROSS-REFERENCE TO RELATED APPLICATIONS

This application claims priority to U.S. Patent Application Ser. No. 62/277,547 which was filed on Jan. 12, 2016 and International Patent Application No. PCT/US2017/013170 which was filed on Jan. 12, 2017. The contents of the above applications are incorporated herein by reference in their entirety.

FIELD OF THE INVENTION

This document relates generally to electronic barcoding of particles or micro-particles for multiplexed assays.

BACKGROUND

Barcoding of micro-particles is one of the most common approaches for enabling multiplexed molecular assays. Thus far, optical and plasmonic methods for barcoding particles have shown the most promise. The primary difficulty with this type of barcoding is the large and bulky instrumentation required for performing the readout, which is unsuitable for applications where portability is needed.

It has been demonstrated that both continuous flow lithography and stop-flow lithography (a) can be used for synthesizing dot-coded multifunctional particles bearing millions of unique codes and (b) are applicable to both nucleic acid and protein detection. Also, free-floating structural coloured particles have been fabricated with multi-axis rotational control using a colour-tunable magnetic material. Such particles have demonstrated applicability to nucleic acid detection. Oligonucleotide-modified Au nanoparticles encoded with sequences acting as biobarcodes have been used and screened for multiple target proteins simultaneously with fg/ml sensitivity. Reporter tags have also shown promise for multiplex detection of proteins and nucleic acids. Quantum dot bio-barcodes have demonstrated wide utility in multiplex protein and nucleic acid assays. One of the most widely used commercial solutions for multiplexed detection of proteins and nucleic acids is the Luminex platform, which uses color-coded fluorescent magnetic micro-spheres for multiplexing capability. Recently, a portable CMOS magnetic spectrometer has been designed for demonstrating a "multicolored" magnetic sensing scheme utilizing frequency-dependent information of magnetic beads. Traditionally, impedance based multiplexing of beads can only be performed by using different bead sizes, however due to bead aggregation and manufacturing variations, significant overlaps in measured impedances significantly limits the amount of multiplexing possible to a handful of beads.

SUMMARY

The present disclosure concerns systems and methods for electronic barcoding of particles. In some scenarios, the methods comprise: performing operations by a spin coater to spin coat a single layer of particles onto a substrate; performing operations by a heat applicator to apply heat to the substrate so as to evaporate a liquid; and performing operations by at least one material depositor to transform the particles into electronically barcoded particles. The electronically barcoded particles are formed by: coating a portion of each said particle of the particles with a first conductive layer (e.g., gold); depositing an insulative layer (e.g., aluminum oxide) on the first conductive layer; and/or depositing a second conductive layer on the insulative layer so as to form a parallel plate capacitor on the particle. The parallel plate capacitor is tuned so that the particle has a capacitance that is different than the capacitances of other ones of the electronically barcoded particles.

In those or other scenarios, electron beam evaporation is used to coat the particle with the first conductive layer. Atomic layer deposition is used to deposit the insulative layer on the first conductive layer. Sound energy is applied to the substrate to agitate the electronically barcoded particles for suspending the electronically barcoded particles in a fluid. Thereafter, a multi-frequency impedance analysis is performed of the electrically barcoded particles. For example, an impedance-based flow cytometry is performed using the electronically barcoded particles suspended in the stream of fluid. The suspended electronically barcoded particles are flowed passed an electronic detection apparatus. In this way, the electronically barcoded particles can facilitate protein detection, biomolecular detection, chemical separation and biochemical separation. Additionally or alternatively, the eletronically barcoded particles and multi-frequency electrical impedance spectroscopy are used to differentiate between types of particles which have been electronically barcoaded.

In other scenarios, the methods for providing electronic barcoding of particles comprises: performing operations by a spin coater to spin coat a single layer of particles onto a substrate; performing operations by a heat applicator to apply heat to the substrate so as to evaporate a liquid; performing operations by at least one material depositor to transform the particles into electronically barcoded particles. The electronically barcoded particles are formed by: coating a portion of each particle of the particles with a first material layer; and depositing a second material layer on the first material layer. The dielectric constants and thicknesses of the first and second material layers are selected to provide a unique impedance associated with each the particle. The first and second material layers can be formed of the same or different material (e.g., oxide or other insulative material).

The present disclosure also concerns systems and methods for detecting particle types. The methods involve: using eletronically barcoded particles and multi-frequency electrical impedance spectroscopy to differentiate between types of particles. Each of the eletronically barcoded particles comprises: a surface and a barcode structure disposed on the surface. The barcode structure comprises: a first material layer coating a portion of the surface; and a second material layer disposed on the first conductive layer. The dielectric constants and thicknesses of the first and second material layers are selected to provide a unique impedance associated with each said eletronically barcoded particle.

The present disclosure also concerns an apparatus. The apparatus comprises: a decoupled digital protein detection module causing electrically barcoded particles to interact with other particles through a sandwiched analyte (e.g., protein of interest); an impedance sensor detecting electrical impedances of the electrically barcoded particles passing thereby when suspended within a fluid; a micro-fluidic channel formed between the decoupled digital protein detection module and the impedance sensor and through which the fluid flows; and a micro-fluidic pump (e.g., a magnetic micro-fluidic pump stimulating peristaltic action) configured to cause the fluid's flow through the micro-fluidic channel. The eletronically barcoded particles and multi-frequency electrical impedance spectroscopy are used to differentiate between types of particles which have the electronically barcoaded particles attach thereto. The electronically barcoded particles are used for protein detection, biomolecular detection, chemical separation and biochemical separation.

DESCRIPTION OF THE DRAWINGS

Embodiments will be described with reference to the following drawing figures, in which like numerals represent like items throughout the figures.

DETAILED DESCRIPTION

Figure 1:
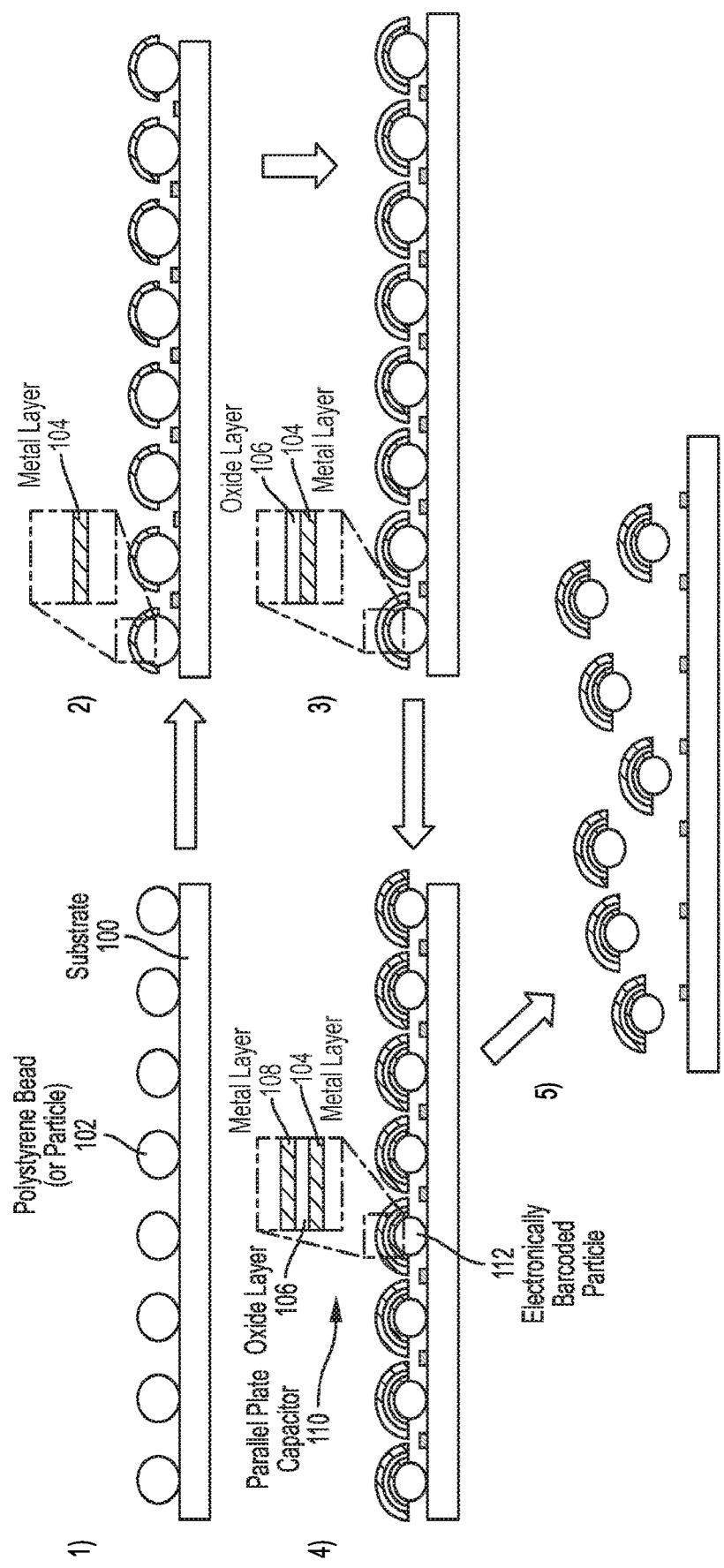
FIG. 1 is a schematic illustration that is useful for understanding a top-down fabrication technique for depositing tunable nano-capacitors on the sides of particles or micro-particles with different capacitances.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout the specification may, but do not necessarily, refer to the same embodiment.

Furthermore, the described features, advantages and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment", "an embodiment", or similar language means that a particular feature, structure, or characteristic described in connection with the indicated embodiment is included in at least one embodiment of the present invention. Thus, the phrases "in one embodiment", "in an embodiment", and similar language throughout this specification may, but do not necessarily, all refer to the same embodiment.

As used in this document, the singular form "a", "an", and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to".

Multiplexed impedance cytometry is an important technique for disease diagnose, since the different kinds of proteins and molecules are different bio-makers providing indications of human health. Compared to other methods such as chemistry reactions and optical measurement, the electronics detection has advanced as being a non-invasive, repeatable, and label-free technique, which can be easily integrated on a single chip. The main drawback of electronical detection is the impedance cytometry, which suffers from the sensitivity of the measurement that is determined by the dimension of the micro-fluidic channel and the material and diameter of the passing molecules. Several previous works have been done for improving the detection precision using an interdigitated electrode pattern and some other device structure. However, even with the featured patterns, the impedance cytometry still experiences the difficulties to show the differences of the molecules in a similar diameter and material.

The key fabrication process of the technique is that coating 1-100 nanometer layers on the top half of the molecules with a metal material or a metal and metal oxidized material using electron beams and an atomic layer deposition technique. These surface modified molecules (also referred to herein as Janus particles) have the impedance differences over a wide frequency band. The transit frequency (which indicates the conductive or resistive property for the molecule) of the electronically barcoded particles is determined by the surface modification while other factors such as the material, diameters of the molecules are negligible. During the measurement, the impedance information is acquired by the lock-in amplifier with multi-frequency at the same time.

The present solution described herein comprises a novel modality for electronically barcoding particles or micro-particles. The barcoded particles or micro-particles can be used in a plurality of different applications. These applications include, but are not limited to, protein detection, biomolecular detection, chemical seperations, and biochemical seperations (e.g., such as in in the petroleum industry). In these applications, the barcodes are used to identify types of particles contained in a fluid. This particle type identification faciliates protein detection, biomolecular detection, chemical seperation and biochemical separation.

Figure 2:
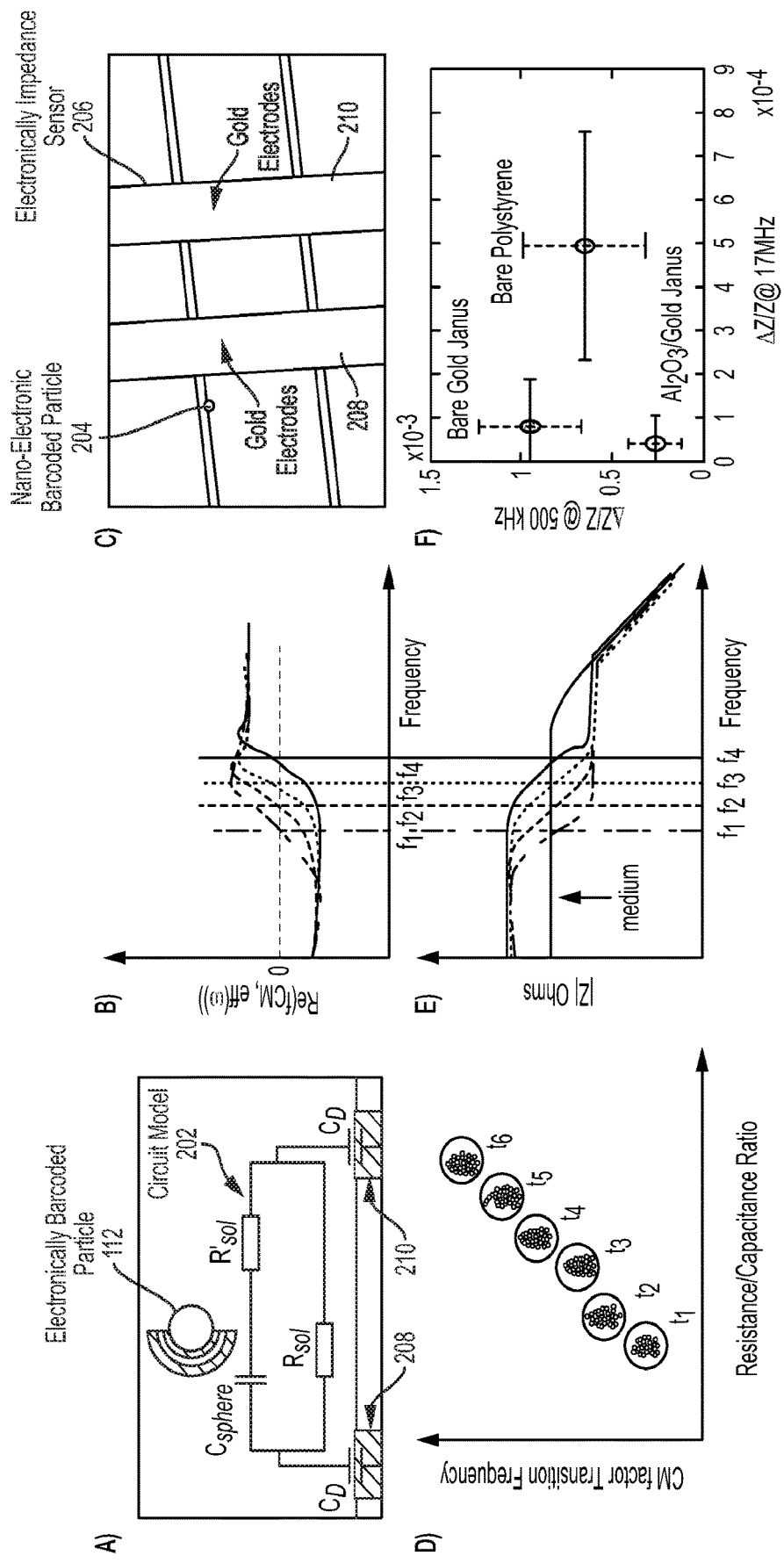
FIGS. 2A-2F (collectively referred to as "FIG. 2") provide schematic illustrations that are useful for understanding a multi-frequency impedance analysis of barcoded particles or micro-particles.
Figure 6:
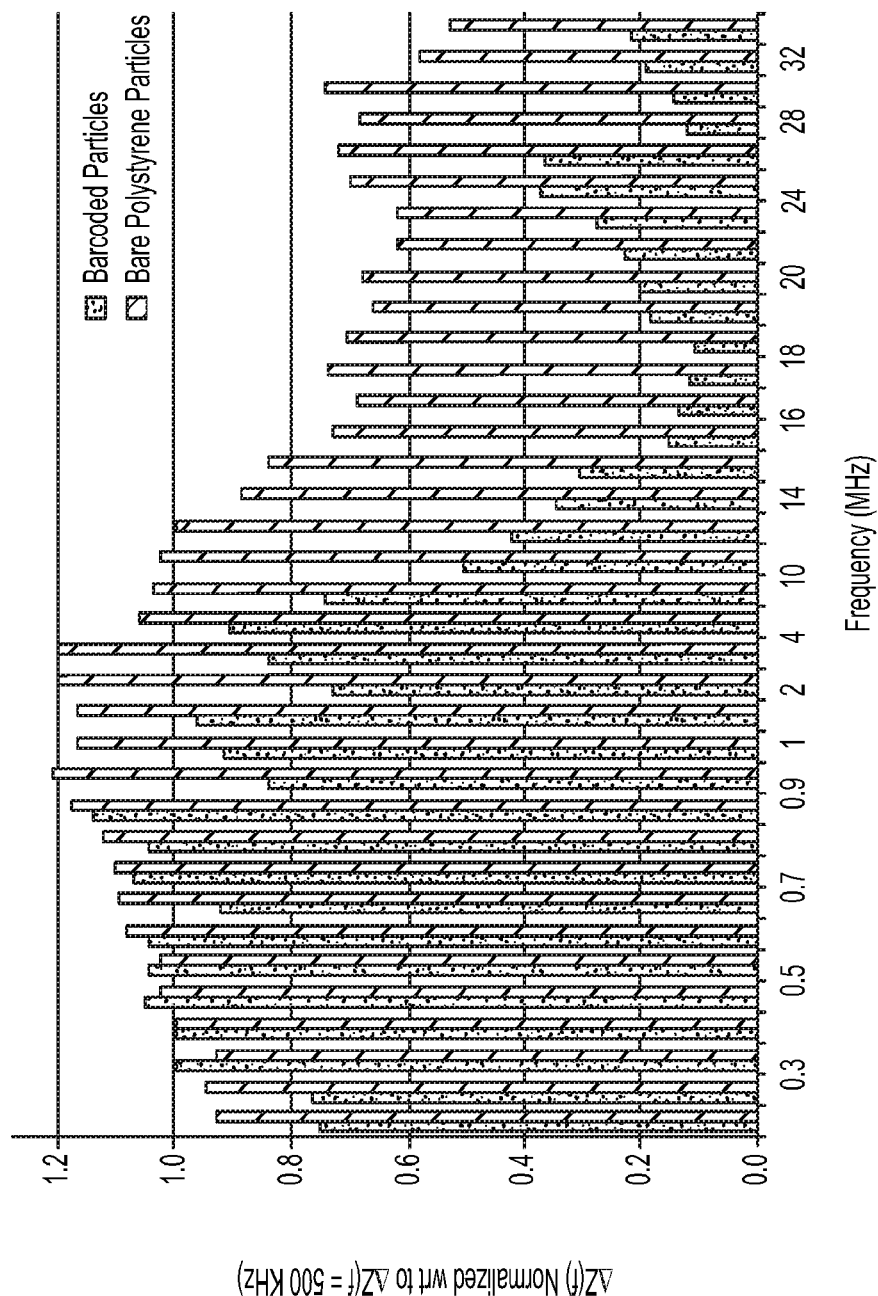
FIG. 6 comprises a graph that is useful for understanding an average ensemble of peaks for multi-frequency impedance of barcoded particles and bare polystyrene particles.

Accordingly, the present solution involves: fabricating nano-capacitors on the sides of particles or micro-particles; and using multi-frequency electrical impedance spectroscopy and special signal processing algorithms for differentiating between various particle types. Spectroscopy involves obtaining measurements of spectra produced by the electrically barcoded particles when they interact with electromagnetic radiation. Spectroscopy is well known in the art, and therefore will not be described in detail here. However, it should be understood that the Spectroscopy employed herein to detect different types of particles involves (as shown in FIG. 2 and FIG. 6) measuring the impedance of the particles (or beads) at multiple frequencies simultaneously to capture the broad frequency spectrum of each barcoded particle (or bead) instantaneously. The relationship between the impedances at the different frequencies allows for differentiating one particle (or bead) barcode to another.

The present solution distinguishes from conventional techniques for barcoding particles in that it barcodes particles electronically as opposed to optically, magnetically and plasmonically. The results of the present solution include electrically barcoded particles for performing multiplexed detection of biomarkers using multi-frequency impedance flow cytometry. Impedance flow cytometry involves suspending the electronically barcoded particles in a stream of fluid and passing them by an electronic detection apparatus. The electronic detection apparatus is configured to count the electronically barcoded particles that pass thereby and detect the types of the particles which were electronically barcoded. The present solution facilitates the development of point-of-care/portable diagnostic devices.

The present solution can be used in various applications. For example, the present solution can be employed for proteomics applications, transcriptomics applications, genomics applications, glycomics-based diagnostics, and point-of-care diagnostics. The present solution can facilitate: diagnosis of cancer and other diseases; identifications of infectious agents (e.g., bacteria, fungi, parasites, viruses, etc.); drug development (monitoring cytotoxicity, transcriptome, proteaomic); and the provision of a research tool for gene expression, miRNA, rRNA, tRNA, protein expression and protein-DNA interaction analysis. The present solution can also be used for: environmental monitoring; industrial/energy applications (e.g., purification, industrial monitoring, and petroleum industrial monitoring); conjugating barcoded micro-particles to proteins/peptides (e.g., antibodies, protein A, etc.), nucleic acids (e.g., DNA, RNA or nucleic acids with a modified base, etc.); and/or diagnosis of specific diseases/infections. The present solution can be implemented as a kit consisting of pre-conjugated micro-particles, a micro-fluidic device for performing multi-frequency electrical impedance-based flow cytometry, and a signal processing algorithm for differentiating between different barcodes.

Referring now to FIG. 1, there is provided a schematic illustration that is useful for understanding a top-down fabrication technique for depositing tunable nano-capacitors on the sides of micro-particles with different capacitances (or for fabricating electronically barcoded particles). In some scenarios, each capacitance specifies a respective type of particle such that there is a one-to-one correspondence between a barcode and a particle type. The capacitance is tunable by adjusting the thickness of the oxide and/or the dielectric constant of the oxide layer. The thickness of the oxide is selected to provide a desired capacitance and/or electrical impedance associated with the respective particle. Therefore, as mentioned above, the electronically barcoded particles can be employed for protein detection applications, biomolecular detection applications, chemical seperation applications and biochemical separation applications.

The top-down fabrication technique generally involves: (1) spin coating a single layer of polystyrene particles (or micro-particles) 102 on a silicone substrate 100; (2) evaporating a metal layer (e.g., gold) 104 on the top-half of the polystyrene particles (or micro-particles) 102; (3) using Atomic Layer Deposition ("ALD") to coat a thin oxide layer (e.g., $Al_2O_3$, $SiO_2$, $HfO_2$, etc.) 106 on top of the metal layer 104; (4) evaporating a thin film metal layer (e.g., gold) 108 to produce a parallel plate capacitor 110; and (5) ultra-sonicating to re-suspend the polystyrene particles (or micro-particles) 102 in a solution. The parallel plate capacitor 110 is tunable so that each polystyrene particles (or micro-particle) 102 can have a unique capacitance associated therewith. The parallel plate capacitor 110 and tuned capacitance constitutes an electronic barcode as the term is used herein. Thus, a polystyrene particle (or micro-particle) 102 with a coupled tuned parallel plate capacitor 110 is referred to herein as an electronically barcoded particle or micro-particle 112.

Spin coating, ALD and ultra-sonicating are well known in the art, and therefore will not be described in detail herein. Still, it should be noted that the spin coating involves applying a small amount of a coating material to a center of the silicone substrate, which is spinning at a low speed or not spinning at all. ALD involves a thin film deposition technique that is based on the sequential use of a gas phase chemical process. Ultra-sonicating involves applying sound energy to agitate the polystyrene particles for decoupling them from the silicone substrate. These operations can be performing using any known or to be known electron beam evaporator, spin coater, heat applicator, and/or atomic layer depositor.

The present invention is not limited the process described above. The above described fabrication process can be modified in accordance with other barcode structures. For example, in some scenarios, the barcode structure comprises only insulative materials (i.e., is absent of metal layers). In this case, the barcode structure can comprise two or more insulative layers formed of: (a) the same insulative materials with different thicknesses; or (b) different insulative materials with different dielectric constants and/or the same or different thicknesses. Accordingly, the above described process could be modified to replace the evaporation step (2) with ALD process.

Referring now to FIGS. 2A-2F, there are provided schematic illustrations that are useful for understanding a multi-frequency impedance analysis of electronically barcoded particles or micro-particles (e.g., electronically barcoded particle or micro-particle 112 of FIG. 1). FIG. 2A shows an equivalent circuit model 202 for a standard two-electrode impedance sensor 202 with an electronically barcoded micro-particle (e.g., electronically barcoded particle or micro-particle 112 of FIG. 1) in proximity thereto. FIG. 2B comprises a graph showing the real component of a Claussiuss-Mossotti ("CM") factor for electronically barcoded micro-particles with four (4) different thicknesses of oxide layers (e.g., oxide layer 106 of FIG. 1). A difference in oxide layer thickness results in a shift in frequency at which the CM-factor transitions from negative to positive. FIG. 2C comprises a microscopic image of a nano-electronic barcoded particle 204 flowing through the electrical impedance sensor 206. FIG. 2D comprises a graph showing that electronically barcoded particles or micro-particles can be differentiated from each other into separate clusters based on a CM-factor transition frequency and a ratio of measured resistance and capacitance, by performing multi-frequency lock-in amplification measurements. FIG. 2E comprises a graph plotting measured particle impedances versus measured particle frequencies for electronically barcoded particles or micro-particles. The graph of FIG. 2E can be used to determine the CM-factor. The cross-over frequency at which a measured particle impedance is equal to a medium impedance corresponds to the particle frequency at which the CM-factor transitions from negative to positive. FIG. 2F comprises a graph in which experimental data plots a normalized peak of measured particle impedances.

Figure 3:
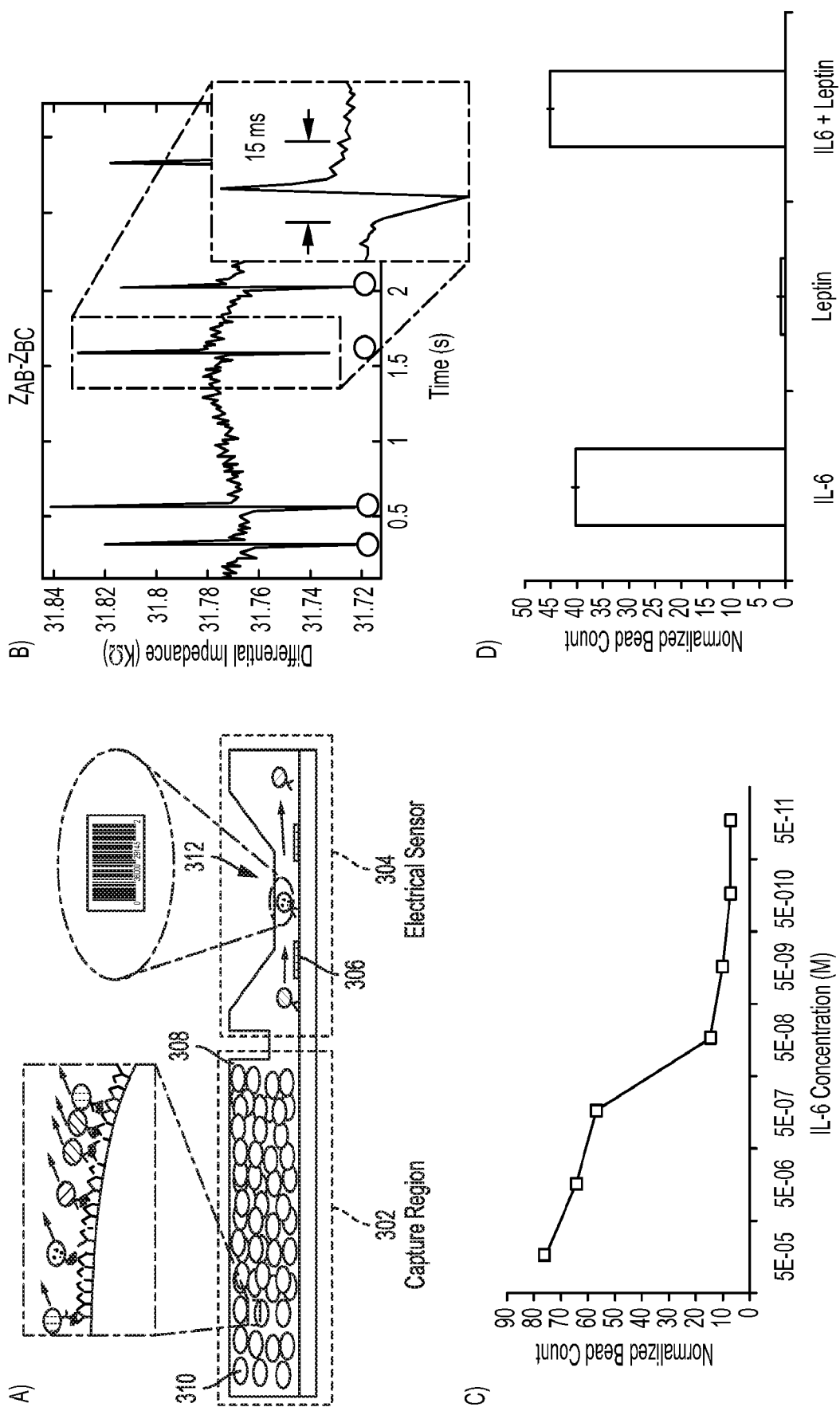
FIGS. 3A-3D (collectively referred to as "FIG. 3") provide schematic illustrations that are useful for understanding a micro-fluidic device.

Referring now to FIGS. 3A-3D, there are provided schematic illustrations that are useful for understanding a micro-fluidic device. FIG. 3A comprises a schematic of a decoupled multiplexed assay. An assay is a test to determine the content or quality of something (e.g., a fluid or piece of metal). A multiplexed assay is a type of assay that simultaneously measures multiple analytes in a single run/cycle of the assay. FIG. 3B comprises a graph showing preliminary data for electronic barcoded particle counting. FIG. 3C comprises a graph of protein titration demonstrating a 10× improvement compared to Enzyme-Linked Immunosorbent Assay ("ELISA"). FIG. 3D comprises a graph showing a particle count in 116 protein spiked in serum with a Leptin concentration 10× higher. High background of Leptin has very little effect on normalized particle count for 116 target protein.

Methodology

The basic principle of the present solution (or multiplexed molecule assay) is the performance of a multi-frequency cytometry measurement of an electronically barcoded particle or micro-particle suspended in a stream of fluid. The multi-frequency cytometry measurement is achieved by passing the electronically barcoded molecule or particle by an electronic detection apparatus. As shown in FIG. 2, the impedance between the two in-plane parallel electrodes 208, 210 would change due to the electrical current flowing through the electronically barcoded particles or micro-particles. The electrodes 208, 210 are respectively connected to an AC voltage supply (not shown in FIG. 2) and a lock-in-amplifier (not shown in FIG. 2). The real and imaginary components of the output voltage of the lock-in-amplifier provides information regarding the complex impedance of the electronically barcoded particles or micro-particles that pass between the electrodes 208, 210.

The barcode structure of an electronically barcoded particle or micro-particle (e.g., polystyrene particle 102 of FIG. 1, electrically barcoded particle 112 of FIG. 2 or nano-electronic barcoded particle 204 of FIG. 2) has a metal layer (e.g., metal layer 104 of FIG. 1) disposed on one half of the particle that is covered by a thin insulative layer (e.g., oxide layer 106 of FIG. 1), similar to Janus particles. The barcode structure's capacitance is tuned by controlling the thickness of the thin insulative layer and the surface area of the particle. This results in modulation of the electrical impedance of the particle at high frequencies.

Janus particles have shown unique physical behaviors in the presence of electric fields with various frequencies in the context of using dielectrophoresis for actuating the particles. This manifests itself as differences in the CM factor. Particularly, the frequency at which the particle transitions from a negative CM factor to a positive CM factor will shift depending on the thickness of the film, as shown in FIG. 2B. The impedance spectrum of the particle also contains information regarding the CM factor. Namely, the transition between positive and negative CM factors corresponds to the point where the impedance of the particle is equal to the impedance of the media. By performing high-speed multi-frequency lock-in amplification measurements on the tuned particles (e.g., polystyrene particle 102 of FIG. 1, electrically barcoded particle 112 of FIG. 2 or nano-electronic barcoded particle 204 of FIG. 2) as they transit across the impedance sensor (e.g., electrical impedance sensor 206 of FIG. 2), one can determine the precise location of the transitions in the CM factor (where CM factor equals zero) and compute both the diameter of the particles and also the capacitive properties, effectively recognizing one particle barcode from another.

Exemplary Electrically Barcoded Particle or Micro-Particle Fabrication

Figure 9:
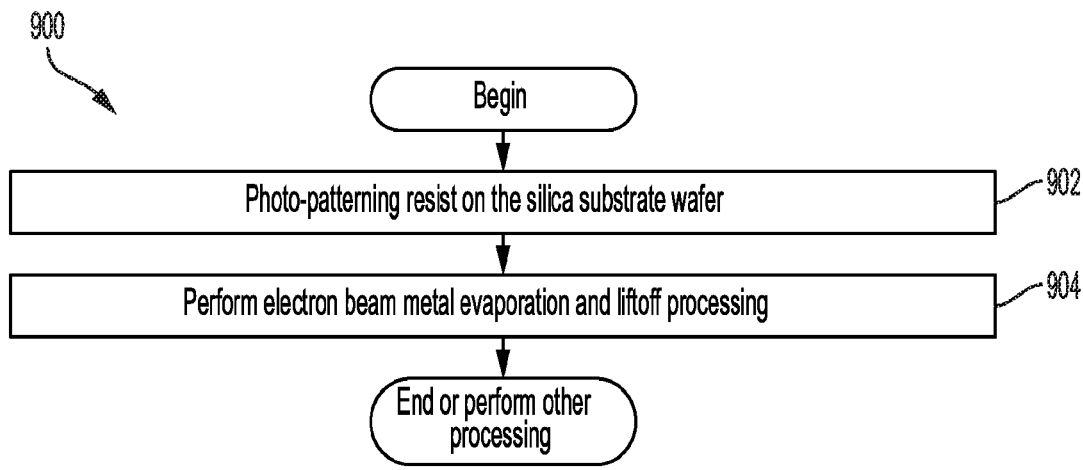
FIG. 9 is a flow diagram of an exemplary fabrication process for sensing electrodes.
Figure 10:
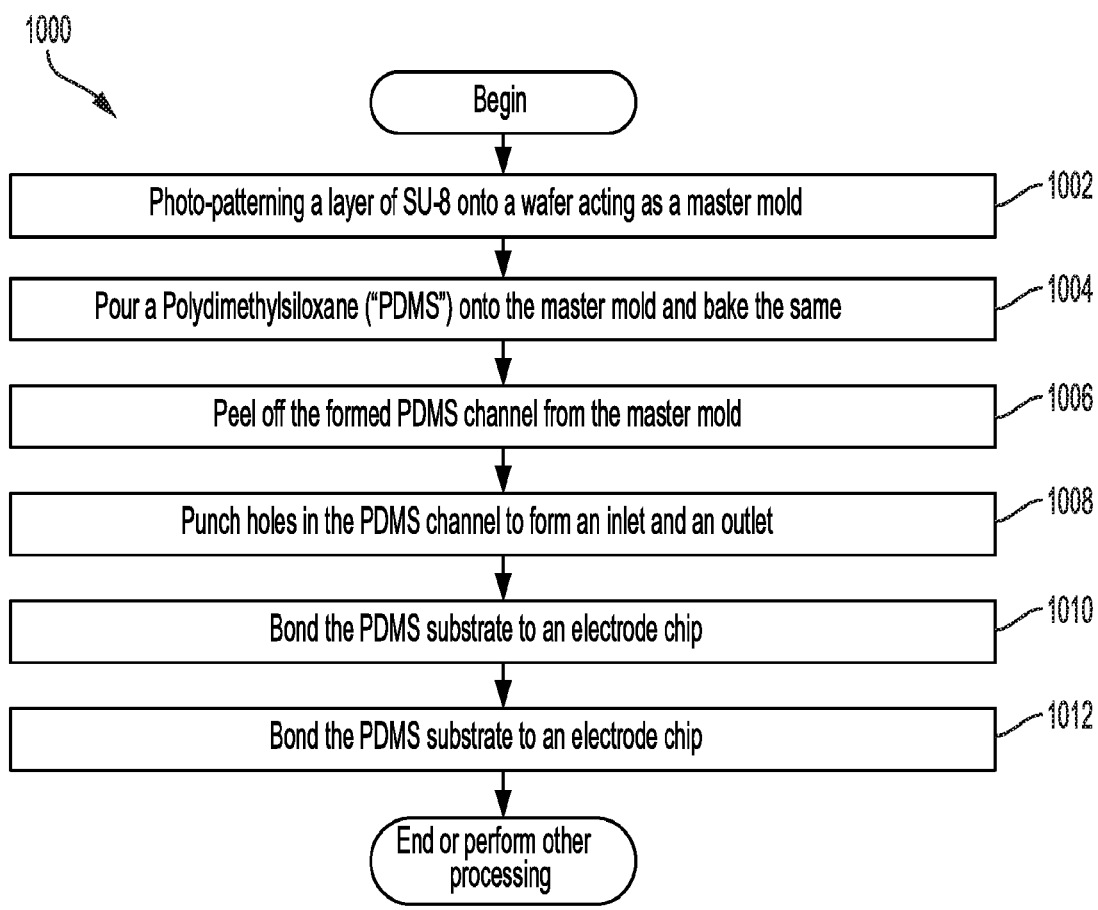
FIG. 10 is a flow diagram of an exemplary fabrication process for forming a micro-fluidic channel in a Polydimethylsiloxane ("PDMS").

Electrically barcoded particle or micro-particle fabrication includes the following three (3) parts: sensing electrodes fabrication; micro-fluidic channel fabrication; and electrically barcoded particle or micro-particle fabrication. In some scenarios as shown in FIG. 9, the fabrication process 900 of the sensing electrodes consists of standard photolithography on a 3" fused silica substrate wafer. This fabrication process begins at 902 which involves photo-patterning resist on the silica substrate wafer, followed by 904 where electron beam metal evaporation and liftoff processing is performed. The photo-patterning process includes wafer cleaning, spin coating of photoresist, soft bake of the photoresist, ultra-violet light exposure through a chromium mask printed on a 4"×4" glass plate, photoresist development, and hard bake of the photoresist. The photo-patterning is followed by electron beam evaporation of a 100 nm gold layer. A 10 nm layer of chromium is used for enhancing adhesion of the gold film to the glass wafer, otherwise the gold film gets peeled off easily. Gold is chosen as the sensing electrode due to its inert nature and resistance to corrosion. However, the present solution is not limited in this regard. Other types of metal can be used for the sensing electrodes.

To fabricate the micro-fluidic channel in a PDMS, a soft lithography is used for patterning. A layer of SU-8 is photo-patterned onto a 3" silicon wafer that acts as the master mold, as shown by 1002. The SU-8 photo-patterning process involves standard photolithography including wafer cleaning, spin coating, soft baking, exposure, development, and hard baking. Afterwards in 1004, the PDMS (10:1 pre-polymer/curing agent) is poured onto the master mold and baked at 80° C., over 2 hours for curing. Once the PDMS channel is formed, it is peeled off from the master mold as shown by 1006. Then in 1008, a 1.5 mm hole and a 5 mm hole are punched to form the inlet and outlet, respectively. The PDMS substrate is then aligned and bonded to the electrode chip in 1010 after both substrates have undergone an oxygen plasma treatment. The bonded chip is then subsequently baked in 1012 at 60° C. for 30 minutes to form the irreversible bond.

Figure 11:
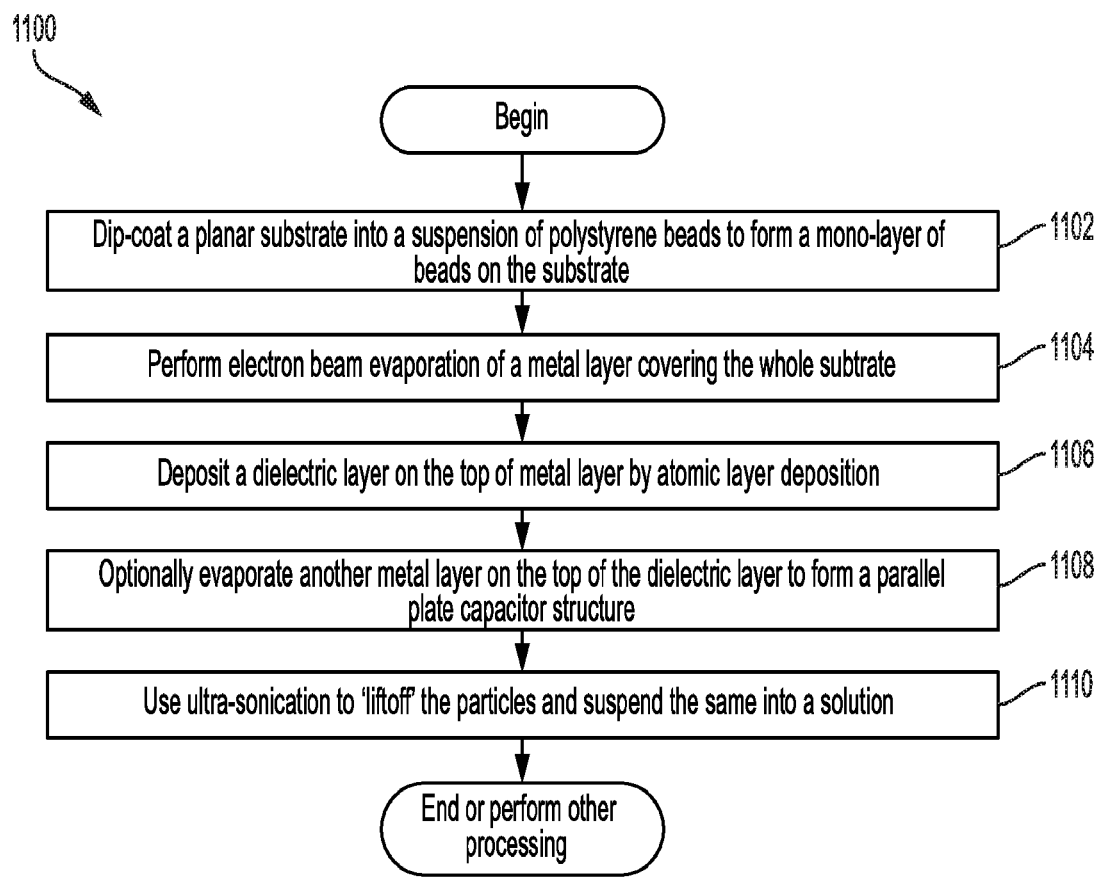
FIG. 11 is a flow diagram of an exemplary fabrication process for electrically barcoded particles or micro-particles.

In some scenarios, the fabrication of electrically barcoded particles or micro-particles consists of 1102-1110 as shown in FIG. 11, which involve: dip-coating a substrate (e.g., a glass slide) into a suspension of polystyrene particles to form a mono-layer of particles on the substrate; performing electron beam evaporation of a metal (e.g., 30 nm gold) layer covering the whole substrate; and depositing an insulative material (e.g., a 10 nm layer of $Al_2O_3$) as the insulator layer on the top of metal layer by atomic layer deposition. Another layer of metal (e.g., gold) can optionally be evaporated on the top of the sample to form a parallel plate capacitor structure as shown by 1108. However, electronic barcoding and impedance based separation can be achieved even without adding the second metal (e.g., gold) layer. The nano-capacitor can be achieved with the first metal layer and the atomic layer deposited insulator layer. Any type of insulating layer can be used to replace $Al_2O_3$. Use of different oxides can also be used as another parameter of barcoding. After the deposition, ultra-sonication is used in 1110 to 'liftoff' the particles from the substrate and suspend the same in the a (e.g., PBS) solution. The complete fabrication process is shown and described in relation to FIG. 1.

The present solution is not limited to the method 1100 shown in FIG. 11. In some scenarios, a plurality of oxide layers is used for electronic barcoding and impedance based separation. In this case, the first metal (e.g., gold) layer is replaced with an oxide layer. Thus, 1104 would be modified to read deposit a first oxide layer on portions of the particles. Optional 1108 may be modified in a similar manner if three oxide layers are employed.

Exemplary Cytometry Experiments

Exemplary cytometry experiments will now be described. The present solution is not limited to the particulars of these exemplary cytometry experiments.

For all experiments, gravity flow was relied on to pump the fluid through the micro-channel without relying on syringe pumps. This required that the channel walls be hydrophilic so that capillary action will allow the fluid to be wicked in easily and not impede the movement of the fluid once in the channel. Thus before every experiment, the bonded micro-channels were treated with oxygen plasma for thirty (30) seconds to make the channels hydrophilic. The channel was then filled with ten times (10×) PBS buffer to preserve hydrophilicity.

The cytometry experiments are conducted at discrete multi-frequency over one hundred kilo-Hertz (100 k) to thirty mega-hertz (30 MHz). Each measurement set contains three (3) different frequencies where five hundred kilo-Hertz (500 kHz) is set as the control frequency. This allows the calibration and normalization of the impedance to correct for any variations which may occur in the baseline level from experiment to experiment. The device is isolated from external electromagnetic interference by placing the biochip in a metal box serving as a faraday cage. This significantly reduces external interference allowing for reliable measurements all the way up until fifty mega-Hertz (50 MHz).

Polystyrene particles, bare gold Janus particles and $Al_2O_3$/gold Janus particles were used as the test sample. All particles have a three micro-meter (3 um) diameter. Data was processed using a drift and de-noising algorithm, which consisted of a third ($3^{rd}$) order Chebyshev band pass filter. Match filtering was used to improve the Signal-to-Noise Ratio ("SNR") of the peaks introduced by the passing particles.

Results of Exemplary Cytometry Experiments

Figure 4:
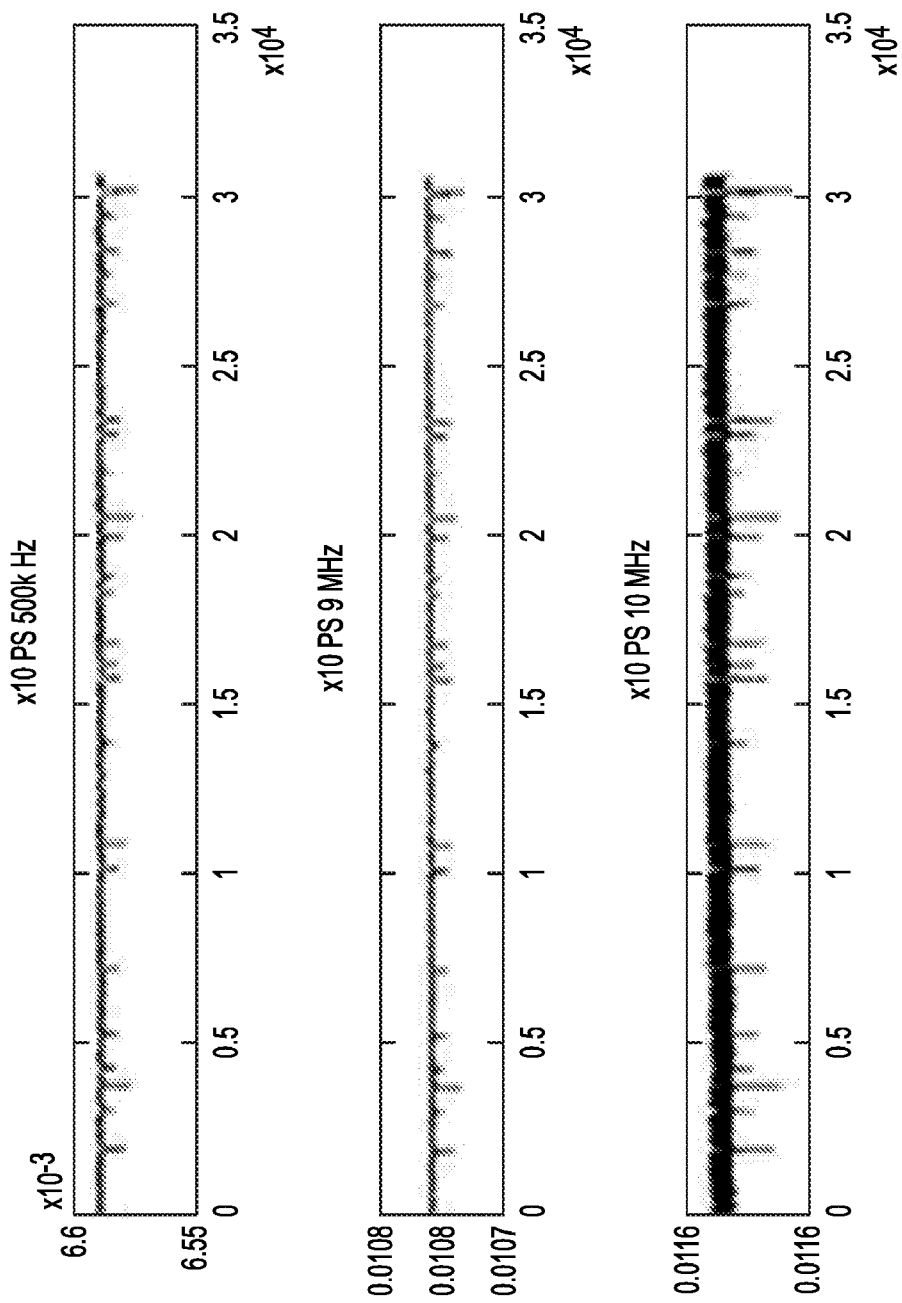
FIG. 4 comprises a plurality of graphs representative of multi-frequency current versus time trace of polystyrene particles at frequencies of five hundred kilo Hertz (500 kHz), nine mega Hertz (9 MHz), and ten mega Hertz (10 MHz).
Figure 5:
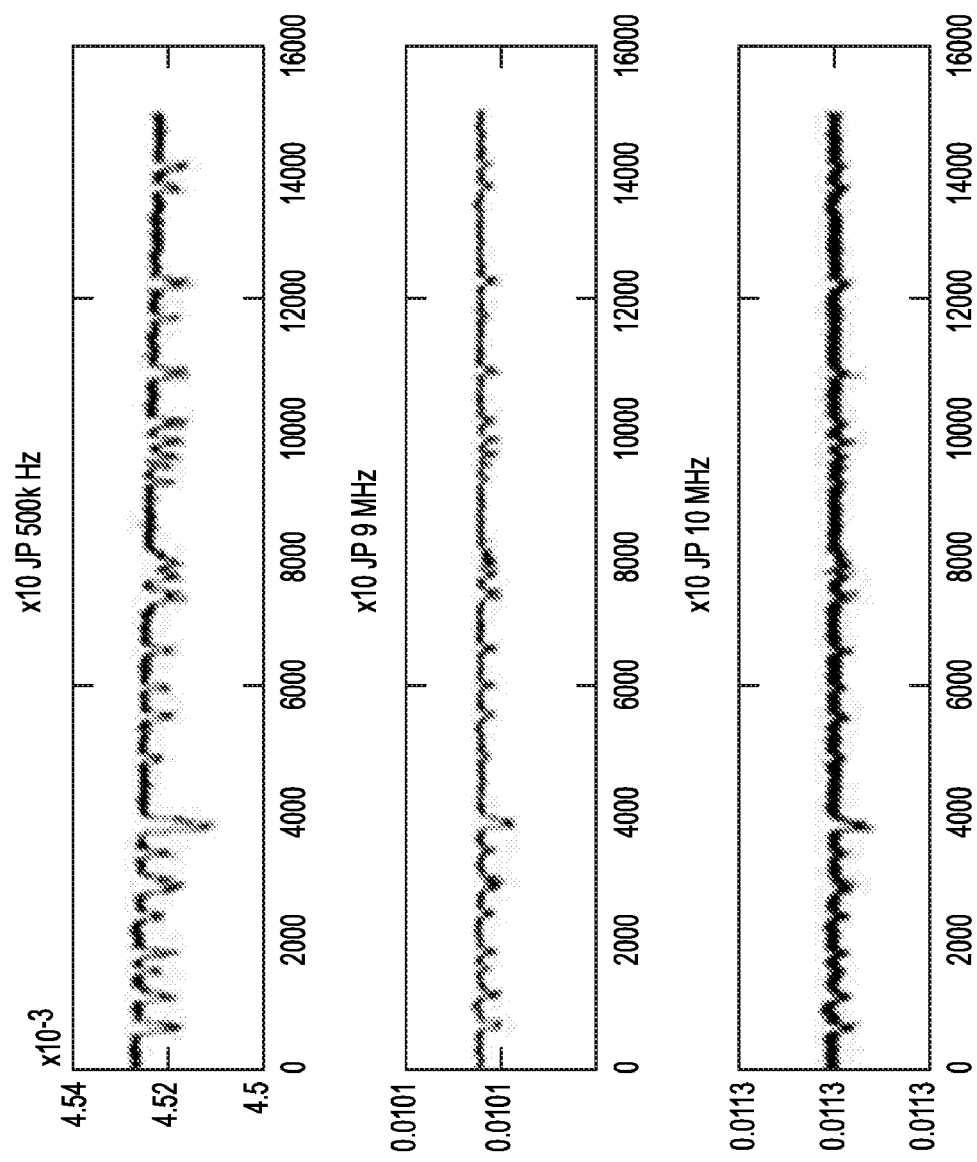
FIG. 5 comprises a plurality of graphs representative of multi-frequency current versus time trace of barcoded particles at frequencies of five hundred kilo Hertz (500 kHz), nine mega Hertz (9 MHz), and ten mega Hertz (10 MHz).

The peak sizes of Polystyrene particles are relatively unaffected by frequency. As shown in FIG. 4, the peaks of nine mega-Hertz (9 MHz) and ten mega-Hertz (10 MHz) are still significant in size. However, for barcoded particles, the peak size decreases with higher frequency, as shown in FIG. 5. At approximately fifteen (15) MHz, the peaks of barcoded particles become buried in noise, while the peak size of the bare polystyrene particles are still significantly greater than noise. Another interesting phenomenon is that the observed peak width of barcoded particles on average is wider than the peak width of polystyrene particles, which may indicate that the barcoded particles are affected by the applied Alternating Current ("AC") electrical field coming from the electrodes due to the dielectrophoresis ("DEP"), while the PS particles experience less DEP force.

FIG. 6 shows a measured frequency behavior over an ensemble of barcoded particles compared with PS particles. Each bar indicates the ratio of the amplitude/baseline at the one frequency specified by x-axis, and the amplitude/baseline at the control frequency five hundred kilo-Hertz (500 kHz) triggered by the exactly same passing particle. In accordance with the plots, the two (2) different kinds of particles are easily distinguishable over the high frequency. Both particles show an SNR drop trend as frequency increases, because at higher frequency the noise (which includes internal fluidic noise and external EM interference noise) is larger than the low frequency. The peak size of the barcoded particles drops much more significantly compared to that of the bare polystyrene particles. The reason is the barcoded particles not only suffer from the noise increment, but also have smaller peak amplitudes due to the CM-factor influenced by frequency. This assumption also matches the results shown in FIGS. 4-5. The noise of ten mega-Hertz (10 MHz) is higher than the noise of five hundred mega-Hertz (500 kHz). The peak amplitude of polystyrene particles is larger than those of barcoded particles.

FIG. 2F shows that when using two-dimensional (2D) clustering, three (3) particle types (e.g., Polystyrene Particle, Bare metal Janus Particle, and Oxide covered Janus Particle) with the exact same diameter can be easily distinguished with each other, despite the fact that the diameters only differ by less than ten nanometers (10 nm). The horizontal axis of FIG. 2F is the peak amplitude/baseline acquired at seventeen mega-Hertz (17 MHz) while the vertical axis is the peak amplitude/baseline acquired at five hundred kilo-Hertz (500 kHz). This is in accordance with FIG. 6, which shows that the maximum peak amplitude/baseline difference of bare polystyrene particles and barcoded particles occurs approximately at seventeen mega-Hertz (17 MHz).

Handheld Battery Powered Ultra-Sensitive Platform

Figure 12:
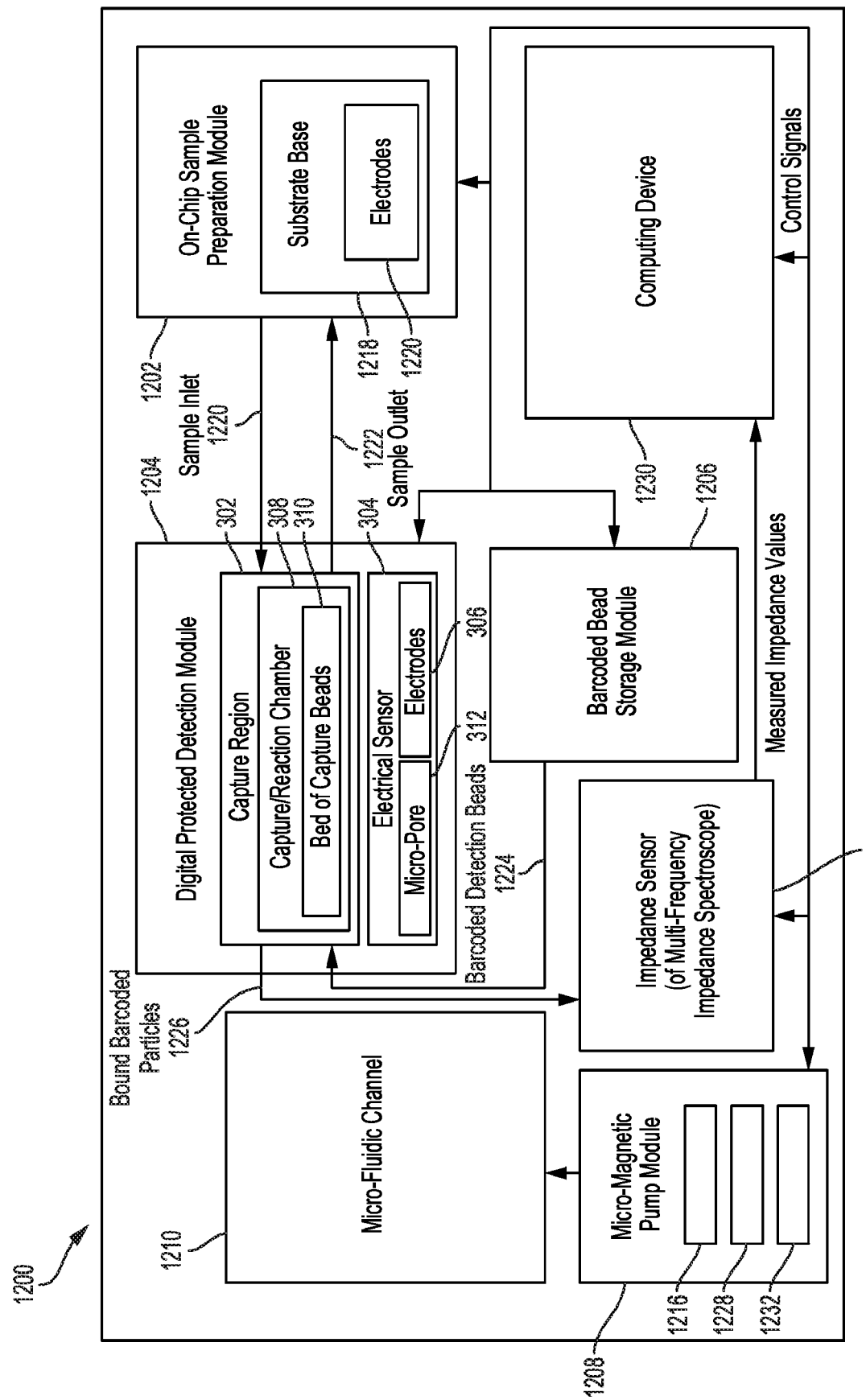
FIG. 12 is an illustration of an exemplary architecture for a handheld battery powered ultra-sensitive platform.

A Handheld Battery Powered Ultra-Sensitive ("HBPUS") platform is provided for multiplexed detection of panels of proteins for environmental and field based monitoring applications. An exemplary architecture for the HBPUS 1200 is provided in FIG. 12. The HBPUS platform 1200 utilizes on-chip sample preparation, particle-based protein concentration, impedance sensing, and micro-magnetic channel actuation for pumping fluids to achieve a fully functional ultra-compact platform. The HBPUS platform 1200 shifts environmental and field-based biological research away from collecting and storing samples and returning weeks to months later in labs to begin analyzing the data, and rely instead on point-of-use on the field analysis of biological samples.

Figure 7A:
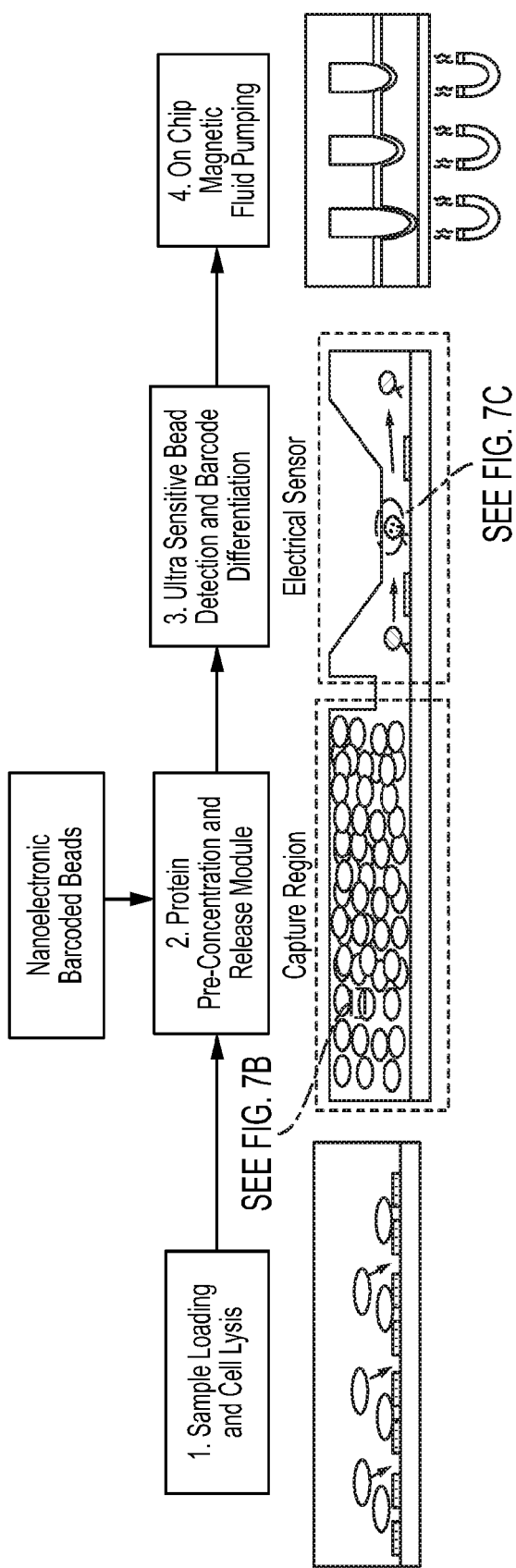
FIG. 7 comprises a schematic illustration that is useful for understanding an overview of an exemplary system implementing the present solution.
Figure 7C:
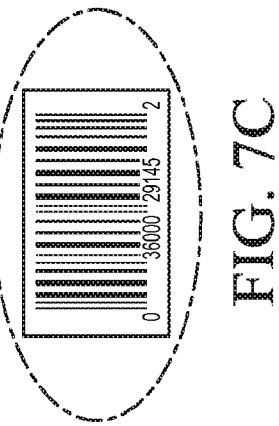
Figure 7B:
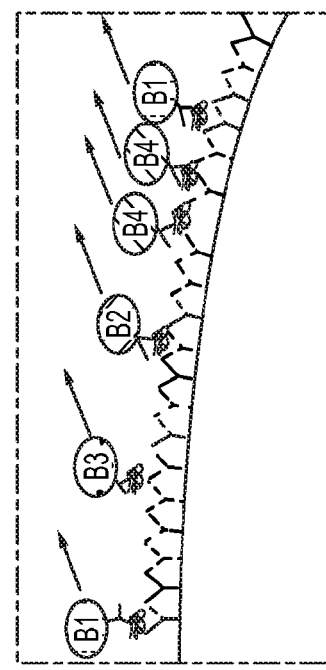

The HBPUS platform 1200 benefits from recent innovations for achieving ultra-sensitivity and low power consumption. Based on such innovations, the key transformative elements (shown in FIGS. 7 and 12) (or key components) of the proposed solution are: (1) a highly efficient on-chip sample preparation module 1202 that uses "ultra-dielectrophoresis" ("U-DEP") for cell trapping and lysis; (2) a digital protected detection module 1204 implementing a highly sensitive low power electronic technique ("decoupled digital protein detection") for quantification of low abundance proteins; (3) a barcoded bead storage module 1206 using the electronic barcoded micro-particles (e.g., those with and/or without metal layers); and (4) an on-chip micro-magnetic pump module 1208 comprising on-chip electro-magnet actuated valves 1216 for fluidic peristaltic pumping to maintain an ultra-compact instrument footprint. Notably, nano-electronic barcoding works by fabricating tunable nano-capacitors on the micro-particle surface as described above, effectively modulating the frequency dependent insulative properties of the particles. Each particle's barcode can be distinguished from another particle's barcode, potentially on the scale of one hundred (100). Multi-frequency lock-in measurements of the real to imaginary impedance ratio allows for particle differentiation.

In some scenarios, the highly efficient on-chip sample preparation module 1202 consists of a substrate (e.g., glass) base 1218 with a channel embedded into a PDMS channel on top. Electrodes 1220 are patterned onto the substrate base using a photolithography process. Photolithography is well known in the art, and therefore will not be described herein. Any known or to be known photolithography technique can be used herein without limitation. Atomic layer deposition is used to pattern nano-meter thick oxide layers to protect the electrodes from corrosion when working at high voltages to get enhanced positive U-DEP. Atomic layer deposition is also well known in the art, and therefore will not be described herein. Any known or to be known atomic layer deposition technique can be used herein without limitation.

In those or other scenarios, the digital protected detection module 1204 has the novel architecture shown in FIG. 3A. The novel architecture consists of two (2) components, namely a capture region 302 and an electrical sensor 304. The capture region 302 includes at least one capture/reaction chamber 308 filled with a bed of capture particles 310 coated with a cocktail of primary antibodies. The electrical sensor 304 consists of a micro-pore 312 sandwiched between two metal (e.g., gold) electrodes 306. During operation of the HBPUS platform 1200, the digital protected detection module 1204 causes electrically barcoded particles (e.g., those with and/or without metal layers) to interact with the captured particles 310 via a sandwiched analyte (e.g., a protein of interest) in the capture/reaction chamber 308. The electrodes 306 provide a means to have an electrical current applied to the fluid in which the electrically barcoded particles are suspended. The electrical current facilitates the detection of electrical impedances of the electrically barcoded particles by the impedance sensor 1250.

The barcoded bead storage module 1206 at least uses the electronically barcoded particles. In this regard, the electronically barcoded particles are stored in a fluid chamber of the particle barcoding module. The electronically barcoded particles are fabricated prior to being stored in the fluid chamber, and are provided to the digital protected detection module 1204 during operation of the HBPUS platform 1200 as shown by 1224 of FIG. 12.

FIG. 2C shows preliminary microscopic images of oxide coated JPs that were fabricated in accordance with this exemplary fabrication procedure. FIG. 2F shows preliminary data demonstrating the difference in impedance between a polystyrene sphere of three micro-meters (3 μm), a three micro-meter (3 μm) bare metal Janus particle, and a three micro-meter (3 μm) Janus particle ALD coated with a ten nano-meters (10 nm) aluminum oxide layer. Even though the particle sizes differ only by twenty nano-meters (20 nm), there is no overlap in normalized particle peak amplitude distribution.

In those or other scenarios, the micro-magnetic pump module 1208 comprises an ultra-compact on-chip micro-pump 1228. The on-chip micro-pump 1228 uses a novel actuation mechanism for deforming PDMS membranes. More specifically, the on-chip micro-pump 1228 stimulates peristaltic action to cause a fluids flow through the micro-fluidic channel 1210. In this regard, a magnetically actuated PDMS valve 1216 fabricated at the top of a micro-fluidic channel 1210 is able to open and close the micro-fluidic channel. The top of the micro-fluidic channel 1210 to be controlled consists of a thin PDMS membrane, on top of which is mounted a micro-patterned soft magnetic layer. By applying a magnetic force at the bottom of the micro-fluidic the soft magnetic material is pulled down, thus deforming the membrane closing the micro-fluidic channel 1210. This idea is advantageous over traditional pneumatic PDMS valves because the valve 1216 can be actuated micro-magnetically thus making the footprint of the whole device ultra-compact, whereas pneumatic valves need either a vacuum source or large and bulky off-chip pumps. Notably, the on-chip micro-pump 1228 stimulates peristaltic action to cause fluid flow, where conventional systems use a syringe to cause the fluid flow. There are many advantages to using the on-chip micro-pump 1228 as opposed to the syringe. For example, the on-chip micro-pump 1228 provides a simpler, cheaper and more compact structural design for causing fluid flow.

Figure 8:
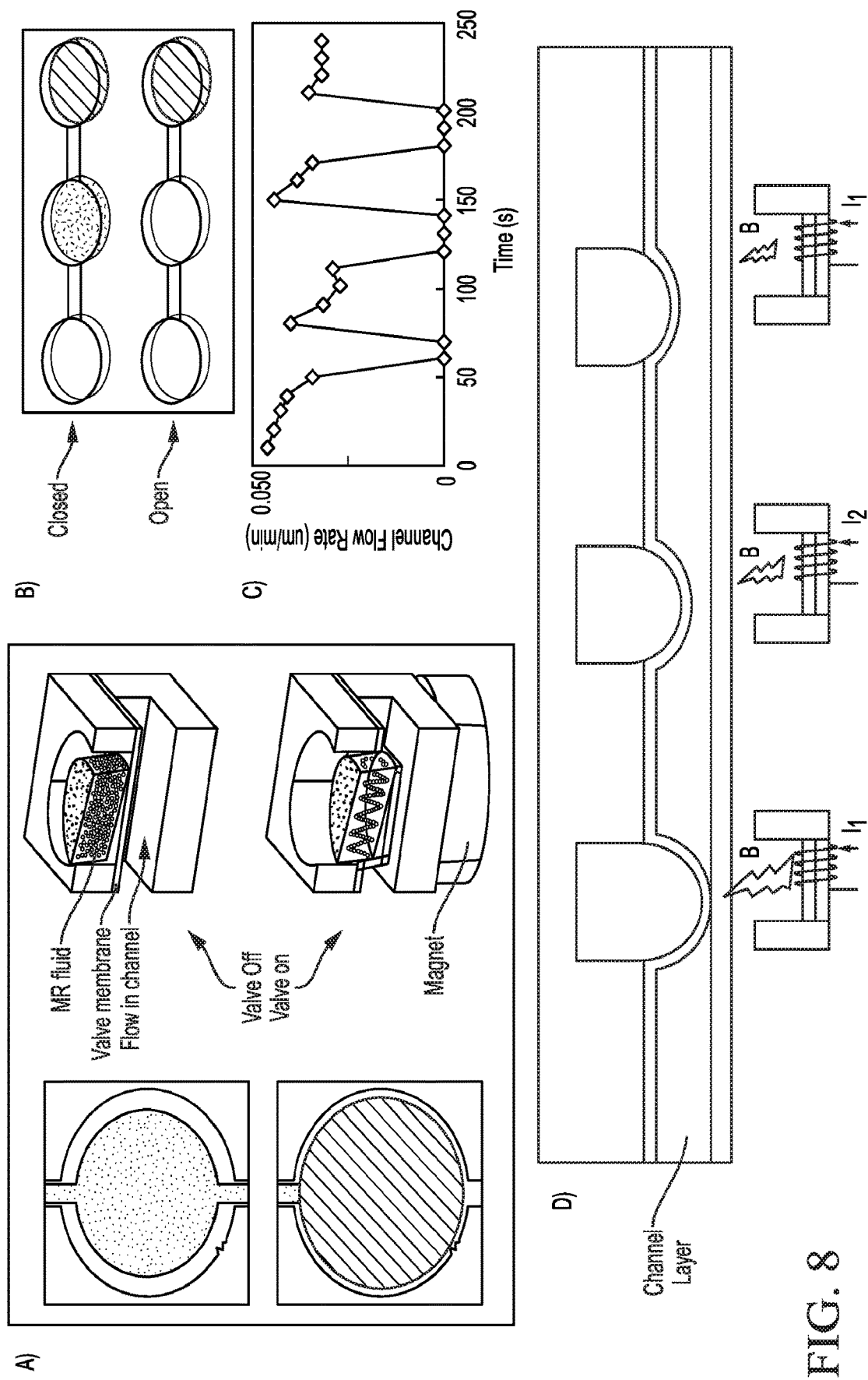
FIGS. 8A-8D (collectively referred to as "FIG. 8") comprise schematic illustrations that are useful for understanding an exemplary micro-valve.

FIG. 8A shows microscopic images of micro-fabricated magnetically actuated PDMS valves 1216 and obtained data demonstrating proof-of-concept for the ability to stop flow using such valves (FIG. 8B). FIG. 8C shows the ability to repeatedly open and close the micro-fabricated magnetically actuated PDMS valves 1216 starting and stopping the flow in the micro-fluidic channel 1210, by switching on and off the magnetic field below the valve.

The ability to instantaneously open and close the micro-fluidic channel(s) 1210 allows a peristaltic pump to be fabricated where three (3) micro-valves are patterned sequentially. Micro-electro-permanent magnets 1232 are mounted below the chip, thus opening and closing the valves 1216 generating peristaltic motion and thus pumping the fluid (FIG. 8D). The frequency of the sequential magnetic actuation controls the flow rate in the micro-fluidic channel 1210.

The micro-fluidic pump 1228 is fabricated by forming a two-layer PDMS channel system, based on the same fabrication process used for the micro-magnetic valve 1216. A thin PDMS membrane spates the two channels. The bottom layer comprises a fluid-flow layer, and the top layer comprises a control layer. Magnetic particles suspended in fluid are injected into the top layer. Micro-post filters are fabricated in the control layer to trap and concentrate the iron particles directly on top of the flow layer. The channels are patterned with soft-lithography.

The four modules 1202-1208 are all formed on a chip. In some scenarios, 3-D printing is used to make a plastic chip holder, Which the chip is mounted on. The chip comprises the four (4) modules 1202-1208 integrated thereon. The chip holder has miniature slots for holding precisely positioned electro-permanent magnets 1232. The fabrication process and geometrical design of the magnets 1232 is optimized to maximize strength to effectively open and close valves, which affects the peristaltic pump 1228 robustness.

During operation of the HBPUS platform 1200, a sample to be analyzed is first injected into the capture/reaction chamber(s) 308 via a sample inlet 1220 and allowed to incubate for a period of time (e.g., several minutes). The bed of capture particles 310 in the capture/reaction chamber(s) 308 serve(s) to increase surface area and capture(s) the efficiency of target proteins flowing through the capture/reaction chambers 308. The capture/reaction chamber(s) 308 is(are) then emptied of the sample via sample outlet 1222. Detection is performed by packing the capture/reaction chamber(s) 308 with smaller barcoded detection particles 1224 coated with a cocktail of conjugate antibodies. The presence of the targets of interest in the sample thus results in the formation of sandwich immuno-complexes, capturing the barcoded detection particles 1224 onto the capture particles 310 within a relatively short period of time (e.g., seconds). Any unbound and non-specifically bound barcoded particles are washed out of the capture/reaction chamber(s) 308, and the specifically bound barcoded particles 1226 are eluted and directed towards the electrical impedance sensor 1250. At the electrical impedance sensor 1250, the specifically bound barcoded particles 1226 are counted and barcode scanned electrically. Each barcoded particle 1226 when passed singly through the active electrodes induces a unique change in the complex impedance. Thus, each peak in complex impedance will both correlate to a specifically bound particle 1226 and its type. In turn, counting the changes in impedance correlate with the abundance of target proteins present in the same.

A library of barcoded particles, tuning particle size, nano-capacitor thickness and insulative layer permittivity is created to sufficiently discriminate between ten (10) different particle geometries suitable for multiplexed protein detection. The library is stored in a data store of a computing device 1230 for use as reference data. The reference data is compared to information collected by the impedance sensor 1250 of a multi-frequency impedance spectroscope. Multivariate analysis allows for identifying clusters which various barcoded particles (or beads) form. This information is stored in the library for training the algorithm on how to classify the particles (or beads). In a test experiment where the multiplex biological assay is performed, impedance of the particles (or beads) is measured at multi-frequency analysis and classified according to their parameters.

By using electronic based solutions for all of the key modules of the HBPUS platform 1200, a significant reduction in the cost and size of the readout instrumentation occurs, thus truly enabling on-the-field analysis. Therefore, the novelty of the proposed solution is three-fold: (1) each of the above-described modules 1202-1208 are original and novel solutions; (2) the modules 1202-1208 are integrated onto a single chip to enable a truly compact portable Micro-Total Analysis ("MTA") system with unmatched performance capabilities; and (3) the performance of the portable MTA system is benchmarked on the field and performs point-of-use quantitative proteomic analysis on environmental samples.

As an example of the research capability of the HBPUS platform 1200, because of "U-DEP" and "decoupled digital detection", it has at least ten times (10×) improvement in sensitivity and ten times (10×) reduction in analysis time compared to ELISA (the gold standard in protein detection). Because of on-chip electromagnet pumping, the HBPUS platform 1200 has a twenty times (20×) reduction in weight and at least a one hundred times (100×) reduction in cost compared to plate readers necessary for doing the optical readout for ELISAs. Because of electronic particle barcoding, the HBPUS platform 1200 potentially has a fifty times (50×) improvement in multiplexing throughput compared to ELISA without adding any extra cost or weight to the platform. The HBPUS platform 1200 may also be equipped with a Global Positioning System ("GPS") capability so that all data acquired can automatically be stamped with precise information regarding the location at which the sample was obtained, making the HBPUS platform 1200 the first ever proteomic tool with a geospatial mapping capability.

Figure 13:
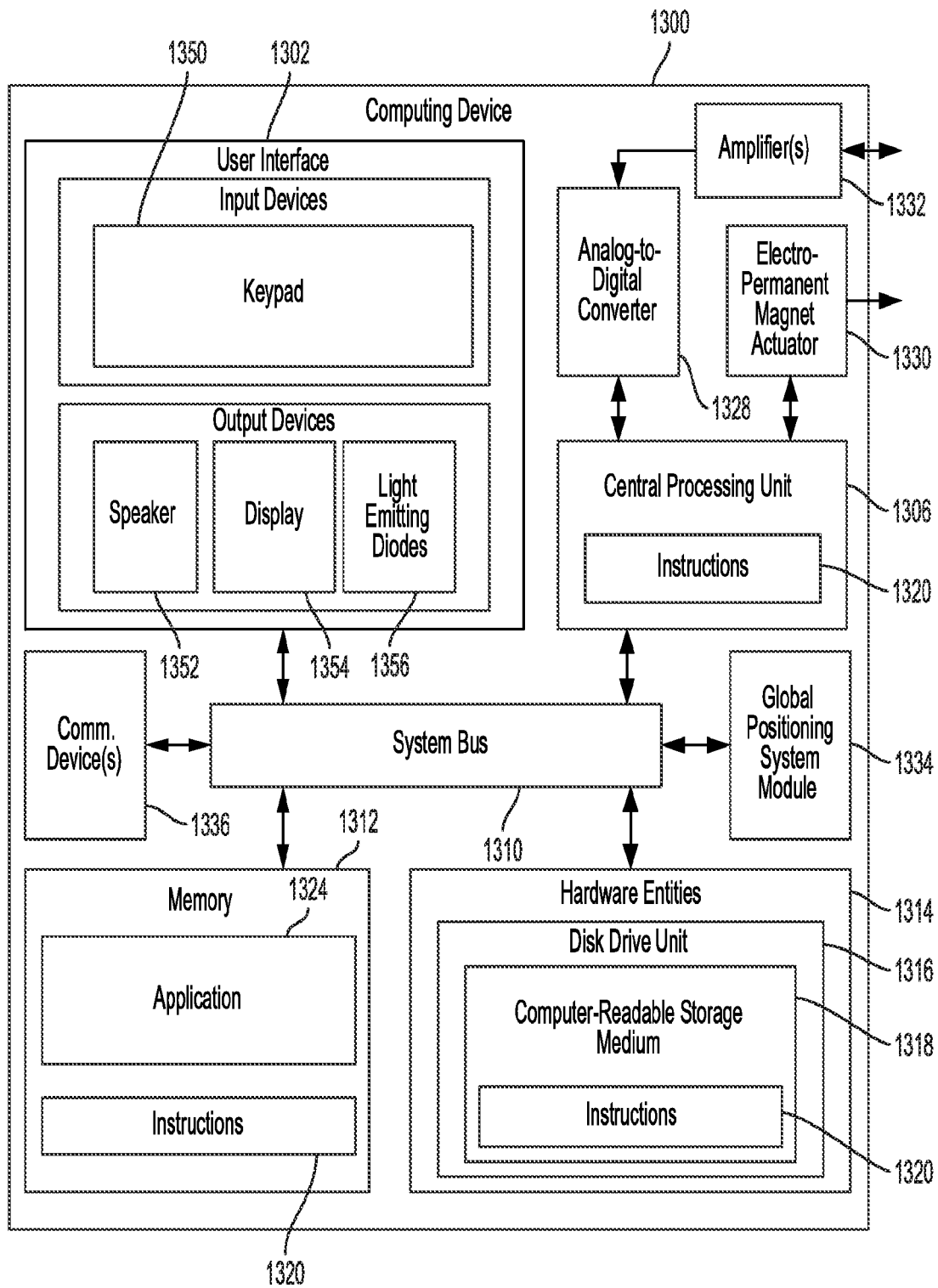
FIG. 13 is an illustration of an exemplary architecture for a computing device.

Referring now to FIG. 13, there is provided a detailed block diagram of an exemplary architecture for the computing device 1300. Notably, the computing device 1300 may include more or less components than those shown in FIG. 13. However, the components shown are sufficient to disclose an illustrative embodiment implementing the present solution. The computing device 1230 of FIG. 12 can be the same as or substantially similar to computing device 1300. As such, the discussion of computing device 1300 is sufficient for understanding computing device 1230.

The hardware architecture of FIG. 13 represents one embodiment of a representative computing device configured to facilitate the fabrication and/or use of electronically barcoded micro-particles for a variety of applications. As such, the computing device 1230 of FIG. 13 implements all or a portion of a method for providing and/or using such electronically barcoded micro-particles in accordance with the present solution. Some or all the components of the computing device 1230 can be implemented as hardware, software and/or a combination of hardware and software. The hardware includes, but is not limited to, one or more electronic circuits. The electronic circuits can include, but are not limited to, passive components (e.g., resistors and capacitors) and/or active components (e.g., amplifiers and/or microprocessors). The passive and/or active components can be adapted to, arranged to and/or programmed to perform one or more of the methodologies, procedures, or functions described herein.

As shown in FIG. 13, the computing device 1230 comprises a user interface 1302, a Central Processing Unit ("CPU") 1306, a system bus 1310, a memory 1312 connected to and accessible by other portions of the computing device 1230 through system bus 1310, and hardware entities 1314 connected to system bus 1310. The user interface can include input devices (e.g., a keypad 1350) and output devices (e.g., speaker 1352, a display 1354, and/or light emitting diodes 1356), which facilitate user-software interactions for controlling operations of the computing device 1230.

At least some of the hardware entities 1314 perform actions involving access to and use of memory 1312, which can be a Random Access Memory ("RAM"), a disk driver and/or a Compact Disc Read Only Memory ("CD-ROM"). Hardware entities 1314 can include a disk drive unit 1316 comprising a computer-readable storage medium 1318 on which is stored one or more sets of instructions 1320 (e.g., software code) configured to implement one or more of the methodologies, procedures, or functions described herein.

The instructions 1320 can also reside, completely or at least partially, within the memory 1312 and/or within the CPU 1306 during execution thereof by the computing device 1230. The memory 1312 and the CPU 1306 also can constitute machine-readable media. The term "machine-readable media", as used here, refers to a single medium or multiple media (e.g., a centralized or distributed database, and/or associated caches and servers) that store the one or more sets of instructions 1320. The term "machine-readable media", as used here, also refers to any medium that is capable of storing, encoding or carrying a set of instructions 1320 for execution by the computing device 1230 and that cause the computing device 1230 to perform any one or more of the methodologies of the present disclosure.

In some scenarios, the hardware entities 1314 include an electronic circuit (e.g., a processor) programmed for facilitating the fabrication and/or use of electronically barcodes particles or micro-particles in accordance with the present solution. In this regard, it should be understood that the electronic circuit can access and run an application 1324 installed on the computing device 1230. The software application 1324 is generally operative to facilitate: particle barcoding; sensor operations; pump operations; electronic readouts; recognition of electronic barcodes; sensor data analysis; and/or particle quantifications. Other functions of the software application 1324 will become apparent as the discussion progresses.

As shown in FIG. 13, the computing device 1230 further comprises amplifier(s) 1332, an Analog-to-Digital ("A/D") converter 1328, an electro-permanent magnet actuator 1330, a Global Positioning System ("GPS") module 1334, and communication device(s) 1336. In some scenarios, all or some of the listed components 1328-1336 are coupled to a Printed Circuit Board ("PCB") which is part of or an accessory to the computing device 1230. PCBs are well known in the art, and therefore will not be described herein. Any known or to be known PCB can be used herein without limitation.

The amplifiers 1332 comprise a lock-in amplifier and a battery powered on-chip amplifier. The lock-in amplifier is configured to perform electronic readouts, barcode recognitions, and particle quantifications. Lock-in amplifiers are well known in the art, and therefore will not be described herein. Any known or to be known lock-in amplifier can be used herein without limitation. The battery powered on-chip amplifier is used to drive the high frequency and high voltage for "U-DEP" force for cell capture.

The CPU 1306 may also be disposed on the PCB. The CPU 1306 is configured for digitally controlling the electro-permanent magnet actuator 1330. The electro-permanent magnet actuator 1330 is configured to actuate the Micro-electro-permanent magnets 1232 of FIG. 12. The A/D converter 1328 digitizes input data (e.g., received from impedance sensor 1250 of FIG. 14 and/or amplifiers 1332) and forwards the digitized data to the CPU 1306. The CPU 1306 may cause the digitized data to be communicated to an external device via communication device(s) 1336. The communications device(s) 1336 include, but are not limited to, a Long Range Communication ("LRC") device and/or a Short Range Communication ("SRC") device. LRC and SRC devices are well known in the art, and therefore will not be described herein. Any known or to be known LRC and/or SRC device can be used herein without limitation. In some scenarios, the SRC device is configured to wirelessly transmit information via a short range technology (e.g., Bluetooth). The external device can include, but is not limited to, a smartphone, a laptop, a desktop computer, a person digital assistant, and/or a server. The data is analyzed and/or stored by the computing device 1230 and/or the external device. The GPS module 1334 is provided for recording the precise location at which the measurement is being performed by the HBPUS platform 1200.

If computing device 1300 is used to fabricate electronically barcoded particles, then it will be configured to control certain external equipment. For example, the computing device 1300 may facilitate the implementation of the described exemplary fabrication procedure for electronically barcoding micron sized particles. Accordingly, the hardware entities 1314 can include an interface for communicating information to and from external devices. Also, computing device 1300 may be configured to control external equipment to: spin coat particles onto a silicon wafer (FIG. 1); heat the silicon wafer to evaporate the liquid; coat the particles with a metal (e.g., gold) layer or an insulative layer (e.g., an oxide layer); deposit an insulative material (e.g., aluminum oxide) using atomic layer deposition; and optionally deposit a layer of metal (e.g., gold) onto the insulative material (e.g., oxide). Therefore, the external equipment can include, but is not limited to, a spin coater, a heat applicator (e.g., a heater), and/or an atomic layer depositor. Electron beam evaporators, spin coaters, heat applicators, and atomic layer depositors (or deposition machine) are well known in the art, and therefore will not be described herein. Any known or to be known electron beam evaporator, spin coater, heat applicator and/or atomic layer depositor can be used herein without limitation. The electron beam evaporator and atomic layer depositor are also referred to herein as material depositors.

Minimizing Particle Aggregation

One issue that can often come up with particle based micro-fluidic assays and electronic sensors is particle aggregation and proteins fowling up the electrodes. If not dealt with properly, particle aggregation can affect target binding and even perhaps flow of the sample. Non-specifically binding is minimized by using optimal surface chemistry, the proper blocking agent both on the particle (Casein) and micro-fluidic channel surface (Bovine Serum Albumin), and optimal surfactant concentration (0.01% Tween). During the above-mentioned exemplary experiments, particle aggregation was effectively minimized to the extent where assay performance and robustness was unaffected. The low cost of the biochips makes them disposable, and also the full assay is rapid (<15 minutes) thus electrode fowling due to protein adsorption over long periods (several hours) of time is not a problem with the HBPUS platform 1200.

Another concern with this assay was the possibility of multiple particles entering simultaneously. At detection limits below the μM range and optimal elution flow rate, this was minimized in the exemplary experiments and the particles flowed through the electronic impedance sensor singly. If multiple particles flowing through the electronic impedance sensor ends up being a problem, DEP or acoustic focusing can be used to force particles to move in a single file line.

Multiplexed Protein Detection Using Barcoded Particles

In the present solution, electronically barcoded micron-sized particles are used. It is believed that this is the first time an impedance based barcoding technique for particles has been proposed with the potential of achieving high barcode density. This will be achieved by fabricating nano-capacitors on the surfaces of the particles. The barcoded structures have two metal layers on one half of the particle separated by a thin insulative layer. The particle capacitance is tuned by controlling the thickness of the oxide and the surface area of the particle. This results in modulation of the electrical impedance of the particle at high frequencies.

A solid-state inorganic insulative material is used herein, as well as ALD to control the thickness of the insulative layer that is sandwiched between the two metal layers. The CM-factor as a function of frequency is directly related to the impedance spectrum of a particle in that the frequencies at which the polarity in CM-factor changes (i.e., where CM-factor equals zero), (FIG. 2B) correspond to the cross over impedance (i.e., where the impedance of the particle is equal to the impedance of the medium (FIG. 3E)). The use of the electronically barcoded micron-sized particles is for protein detection. By performing high-speed multi-frequency lock-in amplification measurements on the tuned particles as they transit across the electrical impedance sensor, a determination can be made as to the precise location of the transitions in the CM-factor (where CM is zero). As a result, both the diameter of the particles and also the capacitive properties can be computed. As noted above, a library of electronically barcoded micro-particles is fabricated that fully characterizes the impedances and responses to tuning the impedances. The library allows one to discriminate between a plurality of (e.g., ten) different particle geometries suitable for multiplexed protein detection.

The circuit model of the electrical impedance of the present solution is shown in FIG. 2A, and consists of a double layer capacitance in series with a solution resistance, which is in parallel with the sphere capacitance. By tuning the capacitance of the particle and performing a multi-frequency lock-in amplification measurement, one can differentiate between different types of particles. By tuning both the size of the particle along with the insulative layer permittivity and thickness, the potential for multiplexing on the scale of one hundred (100) is possible. Different particle sizes with different capacitor thicknesses and different dielectric constants are simultaneously used. Various parameters (e.g., SNR at high and low frequencies, the ratio between real and imaginary impedance, and the crossover point of the CM factor) are measured. Thereafter, a multivariate analysis is performed to identify clusters in order to differentiate between various particle types (FIGS. 2D and 2F).

Notably, the above-described barcoded beads can be used to detect cancer tumors. Rapid quantification of surface markers on Circulating Tumor Cells ("CTCs") can allow for prediction of patient response to various cancer drugs. In this case, an electrical-impedance based biochip can be implemented for quantification of proteins on surfaces of cancer cells. The present assay works by coating magnetic beads with an anti-matriptase monoclonal antibody (M69) that recognizes activated matriptase and then mixing the beads with isolated CTCs. The expression of matriptase on the membrane of CTCs results in bead-CTC aggregation. The use of multi-frequency electrical impedance cytometry allows for differentiating between unbound beads, non-target cells and bead-CTC aggregates. This method can be used for detection and quantification of surface membrane bound protein (i.e., matriptase) levels, as the size and quantity of peaks corresponding to bead-CTC aggregates is proportional to concentration of matriptase expressed on the CTCs.

Figure 14:
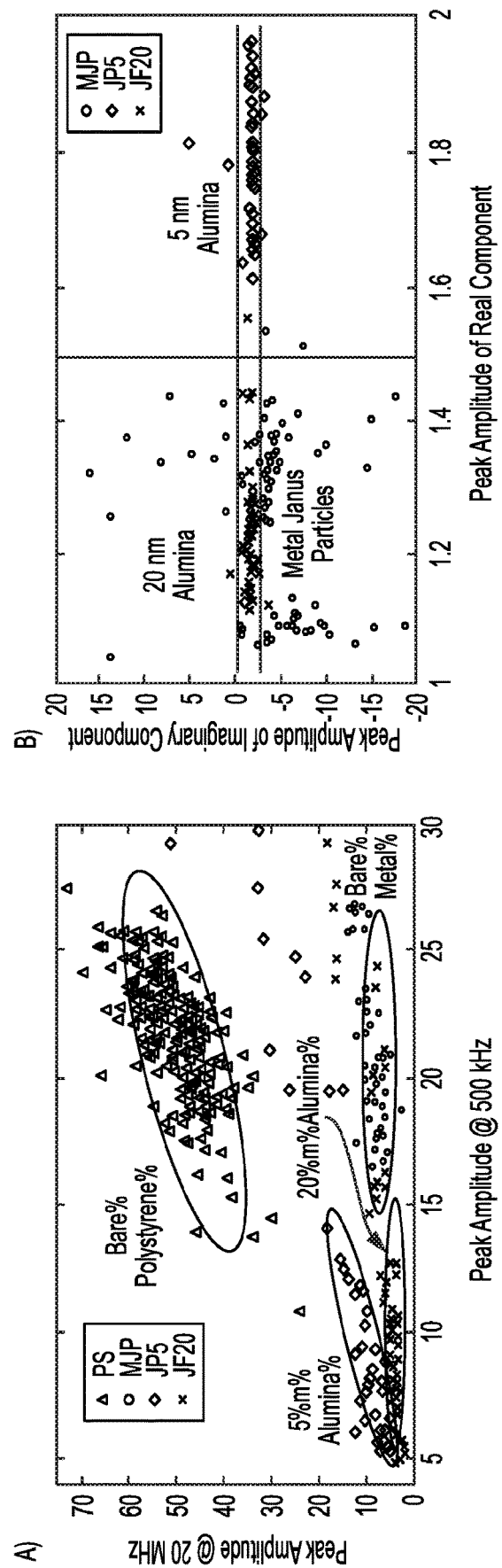
FIG. 14 shows a first graph plotting normalized peak size at 500 Hz vs. normalized peak size at 20M Hz for four different types of particles, and a second graph plotting normalized peak size of Imaginary vs. Real component at 20M Hz for three different types of particles.

Referring now to FIG. 14, there is provided: a first graph plotting normalized peak size at 500 Hz vs. normalized peak size at 20M Hz for four different types of particles; and a second graph plotting normalized peak size of Imaginary vs. Real component at 20M Hz for three different types of particles. These graphs demonstrate the ability to distinguish the difference in between a polystyrene sphere of 3 µm, 3 µm bare metal JPs, and 3 µm JP ALD coated with 5 nm of alumina, and 10 nm of alumina. Even though the particle sizes differ only by 20 nm, there is little overlap in normalized particle peak amplitude distribution. These results demonstrate the feasibility of electronic barcoding as a viable technique for multiplexing.

All of the apparatus, methods, and algorithms disclosed and claimed herein can be made and executed without undue experimentation in light of the present disclosure. While the invention has been described in terms of preferred embodiments, it will be apparent to those having ordinary skill in the art that variations may be applied to the apparatus, methods and sequence of steps of the method without departing from the concept, spirit and scope of the invention. More specifically, it will be apparent that certain components may be added to, combined with, or substituted for the components described herein while the same or similar results would be achieved. All such similar substitutes and modifications apparent to those having ordinary skill in the art are deemed to be within the spirit, scope and concept of the invention as defined.

The features and functions disclosed above, as well as alternatives, may be combined into many other different systems or applications. Various presently unforeseen or unanticipated alternatives, modifications, variations or improvements may be made by those skilled in the art, each of which is also intended to be encompassed by the disclosed embodiments.

I claim:

1. A method for detecting particle types, comprising:
using eletronically barcoded particles and multi-frequency electrical impedance spectroscopy simultaneously to differentiate between types of particles based on detected nanometer scale changes in the diameters of particles, each of the electronically barcoded particles comprising
a surface, and
a barcode structure disposed on the surface, the barcode structure comprising
a first material layer coating a portion of the surface, and
a second material layer disposed on the first material layer;
wherein the dielectric constants and thicknesses of the first and second material layers are selected to provide a unique impedance associated with each said electronically barcoded particle.

2. The method according to claim 1, wherein the first material layer comprises a conductive layer and the second material layer comprises an insulative layer.

3. The method according to claim 2, wherein the conductive layer is gold and the insulative layer is aluminum oxide.

4. The method according to claim 1, wherein the portion of the surface was coated with the first material layer via electron beam evaporation, and the second material layer was deposited on the first material layer via atomic layer deposition.

5. The method according to claim 1, wherein the barcode structure further comprises a third material layer disposed on the second material layer so as to form a parallel plate capacitor on a particle.

6. The method according to claim 5, wherein the parallel plate capacitor is tuned so that the particle has a capacitance that is different than the capacitances of other ones of the electronically barcoded particles.

7. The method according to claim 5, wherein the particle is flowed passed an electronic detection apparatus when suspended in a fluid.

8. The method according to claim 1, wherein a third material layer is disposed on the second material layer, and dielectric constants and thicknesses of the first and third material layers are selected to provide a unique impedance associated with each said electronically barcoded particle.

9. The method according to claim 8, wherein at least one of the first and third material layers is formed of oxide.

\* \* \* \* \*

UNITED STATES PATENT AND TRADEMARK OFFICE
CERTIFICATE OF CORRECTION

Page 1 of 1

PATENT NO.         : 11,099,145 B2
APPLICATION NO.    : 16/069590
DATED              : August 24, 2021
INVENTOR(S)        : Mehdi Javanmard It is certified that error appears in the above-identified patent and that said Letters Patent is hereby corrected as shown below:

In the Specification

At Column 1, Line number 13, enter the following:
STATEMENT REGARDING FEDERALLY SPONSORED RESEARCH
This invention was made with government support under grant number 1556253 awarded by the National Science Foundation. The government has certain rights in the invention.

Signed and Sealed this
Third Day of October, 2023

Katherine Kelly Vidal
*Director of the United States Patent and Trademark Office*